United States Patent
Shelton, IV

(10) Patent No.: US 7,914,552 B2
(45) Date of Patent: Mar. 29, 2011

(54) METHOD OF PERFORMING AN END-TO-END ANASTOMOSIS USING A STENT AND AN ADHESIVE

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 824 days.

(21) Appl. No.: 11/558,215

(22) Filed: Nov. 9, 2006

(65) Prior Publication Data

US 2008/0114466 A1    May 15, 2008

(51) Int. Cl.
    *A61B 17/08*    (2006.01)
(52) U.S. Cl. .................. 606/213; 606/153; 606/154
(58) Field of Classification Search ........... 128/898; 606/153, 154, 213, 214, 215, 8, 149; 602/60, 602/61
    See application file for complete search history.

(56) References Cited

U.S. PATENT DOCUMENTS

| | | | | |
|---|---|---|---|---|
| 1,151,300 A * | 8/1915 | Soresi | | 604/7 |
| 2,453,056 A * | 11/1948 | Zack | | 606/153 |
| 3,774,615 A * | 11/1973 | Lim et al. | | 606/153 |
| 4,214,587 A * | 7/1980 | Sakura, Jr. | | 606/155 |
| 4,379,009 A * | 4/1983 | Shibata et al. | | 156/86 |
| 4,470,415 A * | 9/1984 | Wozniak | | 606/149 |
| 4,693,249 A * | 9/1987 | Schenck et al. | | 606/153 |
| 5,015,253 A | 5/1991 | Mac Gregor | | |
| 5,192,289 A * | 3/1993 | Jessen | | 606/155 |
| 5,254,113 A * | 10/1993 | Wilk | | 606/8 |
| 5,264,525 A * | 11/1993 | Lees | | 525/154 |
| 5,486,187 A * | 1/1996 | Schenck | | 606/153 |
| 5,749,895 A * | 5/1998 | Sawyer et al. | | 606/214 |
| 5,800,522 A * | 9/1998 | Campbell et al. | | 128/898 |
| 5,843,176 A | 12/1998 | Weier | | |
| 5,928,611 A | 7/1999 | Leung | | |
| 5,972,021 A | 10/1999 | Huttner et al. | | |
| 6,211,335 B1 * | 4/2001 | Owen et al. | | 530/350 |
| 6,391,049 B1 * | 5/2002 | McNally et al. | | 606/214 |
| 6,455,064 B1 | 9/2002 | Narang et al. | | |
| 6,575,985 B2 * | 6/2003 | Knight et al. | | 606/149 |
| 6,579,151 B2 | 6/2003 | Tseng et al. | | |
| 6,620,846 B1 * | 9/2003 | Jonn et al. | | 514/519 |
| 6,773,699 B1 * | 8/2004 | Soltz et al. | | 424/78.03 |
| 7,022,131 B1 * | 4/2006 | Derowe et al. | | 623/1.11 |
| 7,078,378 B1 * | 7/2006 | Owen et al. | | 514/7.6 |

(Continued)

OTHER PUBLICATIONS

U.S. Appl. No. 09/430,177, Oct. 29, 1999, Narang et al.

*Primary Examiner* — Julian W Woo
*Assistant Examiner* — Christopher L Templeton
(74) *Attorney, Agent, or Firm* — Frost Brown Todd LLC

(57) ABSTRACT

A method and instruments used to performing an end-to-end anastomosis between two portions of intestinal tissue is disclosed. The method involves drawing a first portion of intestinal tissue over a portion of a bioabsorbable stent. The end of the first portion of intestinal tissue is everted on the stent to create a collar of exposed inner intestinal tissue. A second portion of intestinal tissue is drawn over the stent and over the exposed intestinal tissue. A bandage containing one adhesive compound selected from the group of an adhesive and an adhesive initiator is wrapped about the juncture. The other adhesive compound is applied to saturate the bandage and the combination of an adhesive and an adhesive initiator sets the adhesive to adhere the first portion and the second portion of adhesive to the bandage.

11 Claims, 7 Drawing Sheets

U.S. PATENT DOCUMENTS

| | | |
|---|---|---|
| 7,588,565 B2 * | 9/2009 | Marchitto et al. .............. 606/27 |
| 7,763,041 B2 * | 7/2010 | Bolduc et al. ................. 606/153 |
| 2001/0001827 A1 * | 5/2001 | Chapman ..................... 606/153 |
| 2002/0116018 A1 * | 8/2002 | Stevens et al. ................ 606/153 |
| 2003/0236518 A1 * | 12/2003 | Marchitto et al. .............. 606/27 |
| 2004/0050393 A1 * | 3/2004 | Golden et al. ................ 128/898 |
| 2004/0186489 A1 * | 9/2004 | Lee ............................... 606/153 |
| 2004/0190975 A1 | 9/2004 | Goodman et al. |
| 2005/0043749 A1 * | 2/2005 | Breton et al. ................. 606/149 |
| 2005/0055022 A1 * | 3/2005 | Schubert ........................ 606/49 |
| 2005/0251179 A1 * | 11/2005 | Vargas .......................... 606/153 |

* cited by examiner

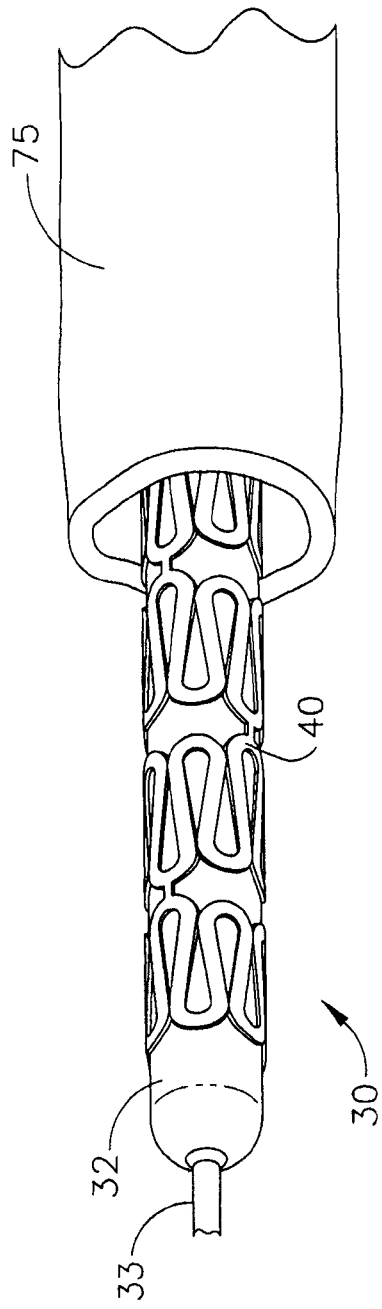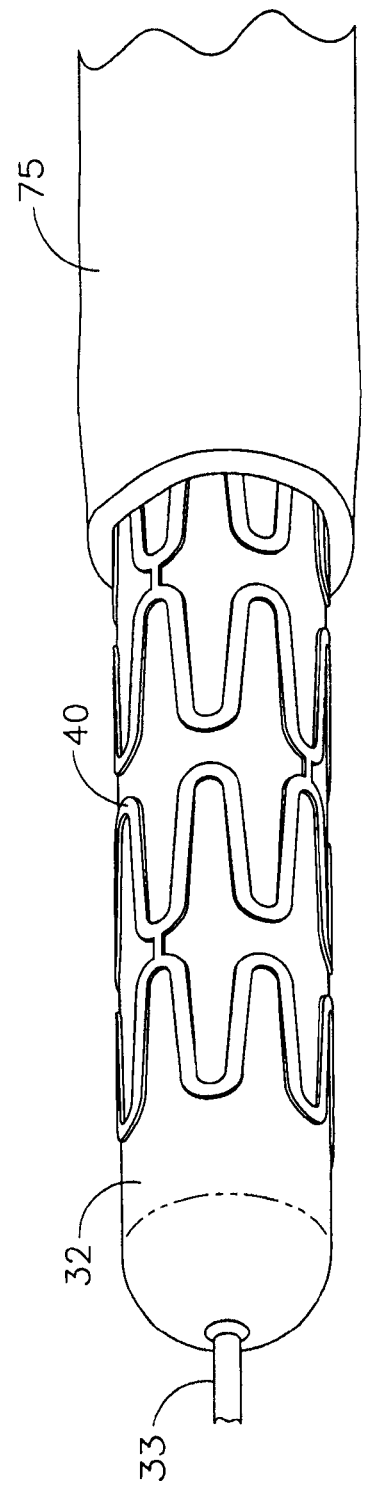
FIG. 2
FIG. 3

METHOD OF PERFORMING AN END-TO-END ANASTOMOSIS USING A STENT AND AN ADHESIVE

FIELD OF THE INVENTION

The present invention relates, in general, to surgical devices and methods for performing an end to end anastomosis of intestinal or bowel tissue, and more particularly to methods of using an adhesive and a stent to perform the anastomosis.

BACKGROUND OF THE INVENTION

Reconnection of two tubular structures (e.g. colon to colon or even colon to stomach) has been a tedious and difficult task. Because of the nature of the material that passes within the colon, contamination containment and leakage prevention are desired. To this end circular staplers have been adopted as a means to quickly reconnect these ends of the colon with one or more concentric rings of staples. Often however the surgeon goes though many steps to insure that there are no leaks in this reconnection. It is not uncommon for dye to be placed into the colon to indicate leaks, or, using pressurized saline to pressure test the staple lines for leaks. If a leak is found, over-sewing the region is a common solution.

Thus, a challenge in joining two pieces of intestinal tissue together in a surgery such as a Duodenojejunostomy, is the reconnection of the two tubular intestinal structures in a leak-proof manner. And if a leak is found, being able to quickly, simply, and easily patch the leak.

Other devices such as stents are used to align and bring together luminal structures such as the intestine. Unlike the rigid stents, intestinal structures are dynamic and use peristalsis to constrict and move intestinal contents. The use of a stent in combination with a material and an adhesive are known such as that taught in U.S. Pat. No. 5,254,113 by Peter Wilk, which is hereby incorporated by reference in its entirety. The collagen based material used by Wilk offers adhesive advantages when used with laser welding but is not porous. Many types of adhesives address the needs of surgery such as adhesives and adhesive initiators disclosed in U.S. Application 20040190975 by Goodman et al. which is hereby incorporated by reference in its entirety.

Consequently, a significant need exists for a method of quickly and easily joining two portions of intestinal tissue together in an end-to-end anastomosis that overcomes the deficiencies of the previous methods, reduces surgical time, offers advantages not available with previous devices and methods, and can restore natural body functions at the surgical site.

BRIEF SUMMARY OF THE INVENTION

The invention overcomes the above-noted and other deficiencies of the prior art by providing a method of creating an end-to-end anastomosis between a first portion of intestinal tissue and a second portion of intestinal tissue. The method comprises a first step of providing a biodegradable stent and a second step of drawing the first and second portions of intestinal tissue together in end-to-end contact over the biodegradable stent. The third step is to wrap the first portion and the second portion of intestinal tissue with a bandage containing an adhesive compound. The adhesive compound is selected from the group of an adhesive and an adhesive initiator. The fourth step is to secure the first portion and the second portion of intestinal tissue together in an anastomosis by saturating the bandage with the other of the adhesive compounds to initiate adhesion of the first portion of intestinal tissue and the second portion of intestinal tissue to the bandage.

In another aspect of the invention, a second method of creating an end-to-end anastomosis between a first and a second portion of intestinal tissue is provided. The method comprises the first step of providing an expandable biodegradable stent and a second step of expanding the stent in at least one of the first and second portions of intestinal tissue. The third step is to evert an end of one of the first and second portions of intestinal tissue on the expanded stent. The fourth step is drawing the end of the other of the first and second portions of intestinal tissue over the everted end to create an overlapping joint. The fifth step is wrapping the overlapping joint with a bandage containing a compound selected from the group of an adhesive and an adhesive initiator. And, the last step is securing the first portion and the second portion of intestinal tissue together in an anastomosis by saturating the bandage with the other compound. The other compound initiates adhesion of the first portion of intestinal tissue and the second portion of intestinal tissue to the bandage.

In yet another aspect of the invention, a third method of creating an end-to-end anastomosis between a first and a second portion of intestinal tissue is provided. The method comprises a first step of providing a stent made from a bioabsorbable material and a second step of drawing the first and second portions of intestinal tissue into end-to-end contact about the stent. The third step is wrapping the first portion and the second portion of intestinal tissue with a bandage made from a bioabsorbable material and containing a bioabsorbable adhesive compound. The bioabsorbable adhesive compound is selected from the group of an adhesive and an adhesive initiator. The last step is securing the first portion and the second portion of intestinal tissue together in an anastomosis by saturating the bioabsorbable bandage with the other of the bioabsorbable adhesive compounds. The other of the bioabsorbable adhesive compounds adheres the first portion of intestinal tissue and the second portion of intestinal tissue to the bioabsorbable bandage.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2 is an isometric view of a portion of the anastomosis device of FIG. 1 shown extending from a first portion of intestine with an unexpanded stent on an inflatable deployment device.

FIG. 3 is an isometric view of the portion of the anastomosis device of FIG. 2 shown extending from a first portion of intestine with the inflatable deployment device partially inflated to partially expand the stent.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
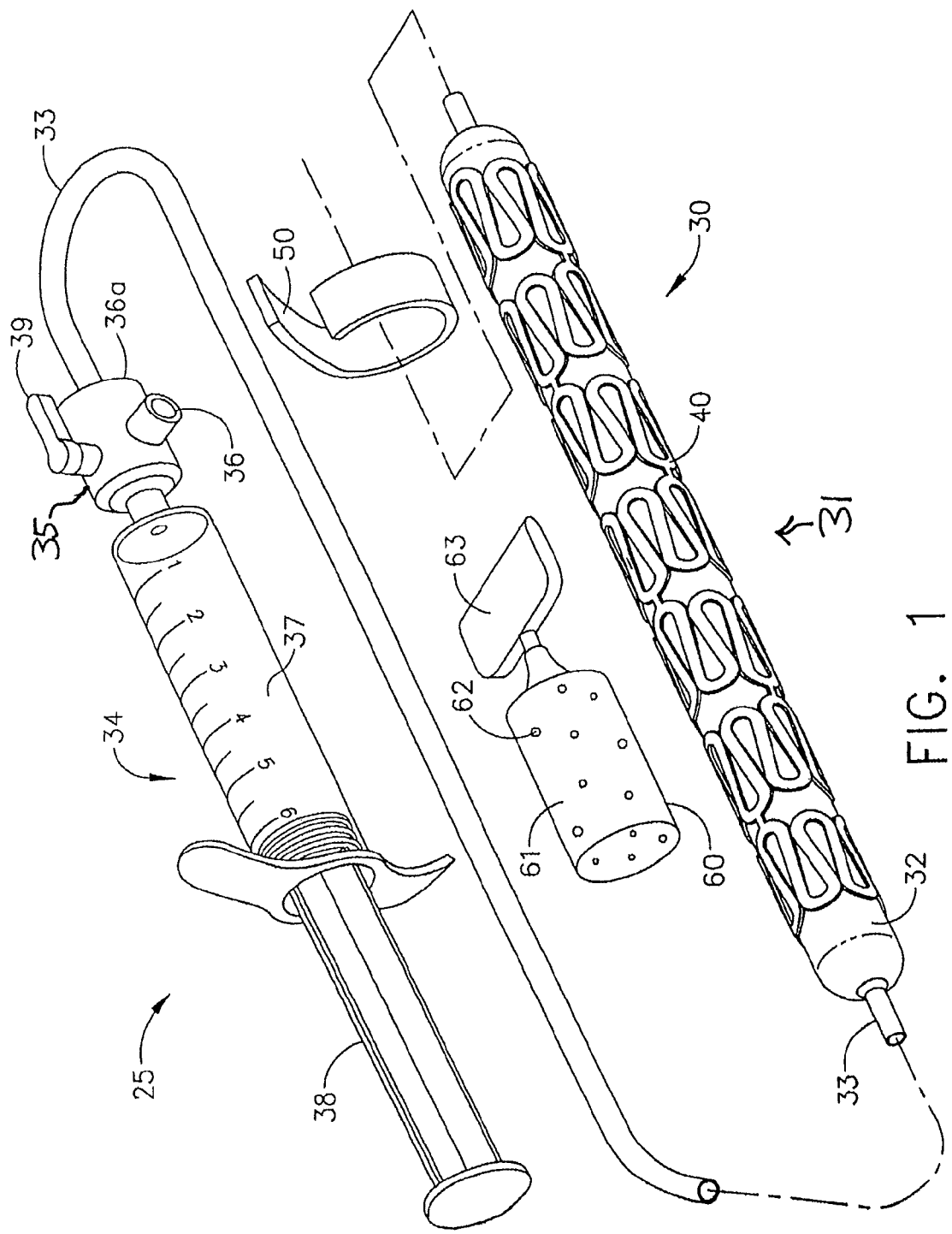
FIG. 1 is an isometric view of the elements of an anastomosis device for performing an intestinal anastomosis.

Turning to the figures, wherein like numerals denote like components throughout the several views, in FIG. 1, an anastomosis device 25 is shown for the end-to-end anastomosis or splicing of two pieces of luminal tissue such as intestinal or bowel tissue. The anastomosis 25 device comprises a stent placement device 30 to place an expandable stent 40 within the of two pieces of luminal tissue, an absorbable material or bandage 50 to wrap around the two pieces of luminal tissue when they are brought into contact over the stent, and a fluid dispenser 60 that for this example, can place a fluid 61 or adhesive 62 onto the bandage 50 to adhere tissue to the bandage. Depending on examples cited below, fluid dispenser 60 can contain a variety of fluids 61 such as an adhesive 62 or an adhesive initiator (not shown), and can include an additive (not shown) in combination therewith.

The stent placement device 30 has a distal inflatable deployment device 31 with an unexpanded stent 40 thereon for insertion into luminal tissue of a patient. The inflatable deployment device 31 comprises a stent expander such as a balloon 32 that is operably attached to a hollow catheter 33 to expand the stent 40 within luminal tissue. A number of devices can expand the stent 40 but for this example, the stent expander is the balloon 32 which can be inflated with a fluid such as a compressable fluid like air, or a non-compressable fluid like water or saline. Hollow catheter 33 extends proximally from the deployment device 31 and operably connects to a proximal pump assembly 34 that pumps fluids therethrough.

Pump assembly 34 can be single stroke or multi-stroke to reduce pumping forces, and has a check valve assembly 35 at a distal end operably coupling the pump assembly 34 to the hollow catheter 33. Check valve assembly 35 comprises a first check valve (not shown) operably coupling pump assembly 34 to catheter 33, and a second check valve (not shown) operably coupled to the orifice 36. Check valves are well known to those skilled in the art, and open to allow one way fluid flow through the check valve, and close to prevent flow in the opposite direction. Check valves can be as simple as a ball and spring, or a deflectable diaphragm or a reed valve. Upon a suction stroke of plunger 38, the check valve assembly 35 allows pump assembly 34 to draw air through orifice 36, past the second check valve, and into a chamber 37, while the first check valve blocks the catheter 33. A compression stroke of plunger 38 closes the second check valve and orifice 36, and opens the first check valve to the hollow catheter 33, enabling fluid to be forced past the valve assembly 34, into the hollow catheter, and into the balloon 32. As plunger 38 moves back for the next suction stroke, the first check valve assembly 35 once again closes off the catheter 33 during the intake stroke to seal the compressed air in the hollow catheter 33 and in the partially inflated balloon 32, and the second check valve opens to draw fluid into the orifice 36 and chamber 37 for the next pressurization stroke. Thus, multiple strokes of the plunger 38 can be used to fully inflate balloon 32 with lower actuation force.

A normally closed rotary release valve 39 is provided on one way valve assembly 35 and when opened, opens a venting passageway 36a (on farside of FIG. 1, not shown) between catheter 33 and the atmosphere to vent or release the fluid within the hollow catheter 33 and inflated balloon 32. The release of fluid back to atmospheric pressure deflates balloon 32. Alternately, by way of example, another fluid such as saline can be used to inflate the balloon 32. Attachment of a saline line to the orifice 36 would enable the saline to be drawn into the pump assembly 34 to accomplish this. Attachment of a vacuum line to venting passageway 36a would draw fluid from and collapse the expanded balloon 32 for easier withdrawal from the expanded stent 40

The anastomosis device 25 also includes a porous or absorbable bandage 50 that can be wrapped around tissue such as luminal tissue, and the fluid dispenser 60 to apply fluid 61 to the bandage 50. For this example fluid 51 is an adhesive 62 that can wick into the bandage 50 and adhere the bandage to luminal tissue. Fluid 51 is sealed in fluid dispenser 60 and can be released by breaking and removing cap 63.

The Stent

The stent 40 is an open tubular shape made from wires or mesh that is expandable from a small diameter cylindrical shape of FIG. 1 to a larger diameter cylindrical shape as shown in FIGS. 3-7. Stents are well known in the cardiovascular art for their initial small size when inserted, ease of use, and ability to create an expanded structure that can hold open blocked luminal structures such as arteries and veins. Stents are also used to hold open lumens in other areas of the body such as the urethra, and the billiary duct. For this invention, the stent 40 can be used to join and hold open two sections of intestine or bowel.

Like the cardiovascular stents, the intestinal stent 40 can be made from any one of a number of materials and can be expanded in a number of ways. The stent 40 must exhibit strength and size characteristics permitting it to be used for intestinal applications. As shown, the stent 40 is made from a tubular metallic structure that has material removed by chemical processes such as photoengraving, or by energy processes such as laser or EDM ablation or cutting. Suitable metallic materials include but are not limited to titanium, phase change alloys such as NITINOL (nickel titanium alloy Naval Ordinance Lab), tantalum, gold, and the like. For this example, the stent 40 is made from a malleable grade of titanium (dead soft) that can be expanded and work hardened by the balloon 39. This example is merely exemplary and other types of materials, tempers, treatments, stent expanders and the like are encompassed by the spirit of the invention.

For example, rather than a dead soft material, stent 40 can be constructed from but not limited to a spring material, a polymeric material, a shape memory alloy, or superelastic alloy.

Each of the examples conform to the spirit of the invention and can require a different stent expander or mechanism suited to enable the stent 40 to expand. By way of example, if stent 40 is constructed from spring materials, the spring properties of the stent itself can expand the stent and the stent expander is a constraint system to hold the stent in an unexpanded position until released. Also by way of example, if the stent is constructed from polymeric materials, the balloon can be the stent expander. And, by way of example, if the stent 40 is constructed from a shape memory alloy, the stent expander can be a heater to cause the expansional phase change, or the shape memory alloy itself which is carefully formulated to undergo an expansive phase change when subjected to body temperatures. Additionally, a balloon stent expander or wedge expander can be used to expand a superelastic stent.

Alternately, stent 40 may be made from any one of a number of suitable biocompatible non-elastomeric materials, such as metal wire, stiff polymeric strands, carbon, ceramic materials, biodegradable materials, or combinations thereof. Metals can also include stainless steel. Of the metals that may be used, titanium or tantalum offer radiopacity and overall flexibility which is characteristic of the low modulus of elasticity of these types of materials. Polymeric materials can include polyesters (such as Dacron) and polyglycolic and polylactic acid (Vicryl).

The stents can be non-absorbable or absorbable by the body. The metallic stents remain within the patient's body for the life of the patient. Absorbable polymeric materials, could be used by the present invention such as but not limited to, polylactic acid (PLA), polyglycolic acid (PGA) and their copolymers, dexon, vicryl, polydioxanone, and polyglyconate. These materials would be absorbed by the body after healing has taken place. Stents are well known in the medical arts, and descriptions of stents, manufacturing processes, and materials can be found in U.S. Pat. No. 5,015,253 to D. MacGregor entitled "Non-Woven Prosthesis" and in U.S. Pat. No. 5,843,176 by S. Weier entitled "Self Expanding Endo-Prosthesis" both of which are hereby incorporated by reference in their entirety.

The Bandage

The bandage 50 is used to wrap around the intestinal splice and to wick up or absorb and hold the adhesive 62 in place. The bandage 50 is biocompatible and may be one or more layers of a porous structure such as a gauze, an open cell foam, a mesh, or any porous structure. Bandage 50 could be constructed from bioabsorbable or biodegradable materials such as polylactic acid, polyglycolic acid, polyglactin, polydioxanone, and polyglyconate. Additionally, by way of example, bandage 50 can be constructed from non-absorbable materials such as but are not limited to metallic materials such as stainless steel, titanium, and gold, and to non-metallic materials such as silk, nylon, polypropylene, braided polyester, polybutester, polyethylene, and polyetheretherketones (PEEK). Bandage 50 could be constructed as an absorbable strip, in layers, have non-permeable barrier layers, contain fluid absorbable or tamponade materials, and be made from any combination of absorbable or non-absorbable materials such as, by way of example, a polylactic acid and polydioxanone mix. The durometer of bandage 50 may be of any durometer making it soft and pliable, to firm or hard for palpability or structure (scaffolding). Bandage 50 by way of example, may be pre-impregnated with or contain compounds or combinations thereof such as but not limited to adhesives 62, additives, and/or adhesive initiators described in greater detail below. Additionally, by way of example, the bandage 50 can increase in volume by having tamponade properties.

Additives can be combined with the bandage 50. For example, the bandage 50 could be impregnated with an adhesive initiator such that when the bandage 50 is in place, the surgeon places an adhesive 62 onto the bandage 50 and the initiator induces polymerization of the adhesive and "sets up" the adhesive 62. Alternately, by way of example, the bandage 50 could be pre-coated with an adhesive 61 and the fluid 61 applied to the bandage could be an adhesive initiator that initiates or "sets up" the adhesive 62 in the bandage. Or, by way of another example, the bandage could contain an alternate radio-opaque additives such as barium and an adhesive initiator. In this example, the fluid 61 in the fluid dispenser 60 is an adhesive 61 that sets up when combined with the adhesive initiator.

The Fluid Dispenser

The fluid dispenser 60 contains a fluid 61 that can induce adhesion of the bandage 50 to the intestinal tissue. Fluid 61 is sealed within the fluid dispenser 60 by a break-away cap 63. Fluid 61 can be an adhesive 62 or an adhesive initiator that can be combined with one or more additives. Fluid dispenser 60 could be made from one or more parts of any one of a number of materials or combinations of materials such as but not limited to, plastic materials including butyrate or polyethylene rubber, silicone or plastic material, such as, for example, polyvinyl chloride, polyethylene, polyurethane, natural or nitril rubber, or any combination thereof.

Adhesives

As described above, the adhesive 62 could be but is not limited to polymerizable and/or cross-linkable materials such as a cyanoacrylate adhesive. The adhesive materials, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an .alpha.-cyanoacrylate. When cross linked or polymerized, the cyanoacrylate can change from a liquid to a solid. Polymerized adhesives for example, can be formulated to be flexible to rigid. If desired, adhesives can be a single part or dual part adhesive, and/or can contain one or more additives. Polymerization of the adhesive 62 can occur from, but is not limited to, exposure to moisture, saline, temperature, or exposure to catalysts such as adhesive initiators.

Adhesive Initiators

Adhesive initiators 65 are for polymerization and/or cross-linking of a polymerizable monomer such as adhesive 62. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25.degree. C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

Particular initiators for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin(II)2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfate, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

Alternately, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt napthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which are incorporated herein by reference.

Additives

If desired, one or more additives can be added or applied to the bandage 50, the stent 40, or the adhesive 62, and the adhesive initiator. These additives can have a number of uses such as therapeutic, medicinal, adhesion enhancers, and the like. Examples of suitable additives include, but are not limited to, anesthetics, sclerotic or necrosing agents plasticizing agents, thixotropic agents, buffers, catalysts, adhesive initiators, fillers, micro particles, thickeners, solvents, drugs, medicaments, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like. Many suitable adhesives 62, adhesive initiators and additives may be found in U.S. Application 20040190975 by Goodman et al. which is hereby incorporated by reference in its entirety. Alternately, one or more additives can coat the stent 40.

Method of Use

Figure 4:
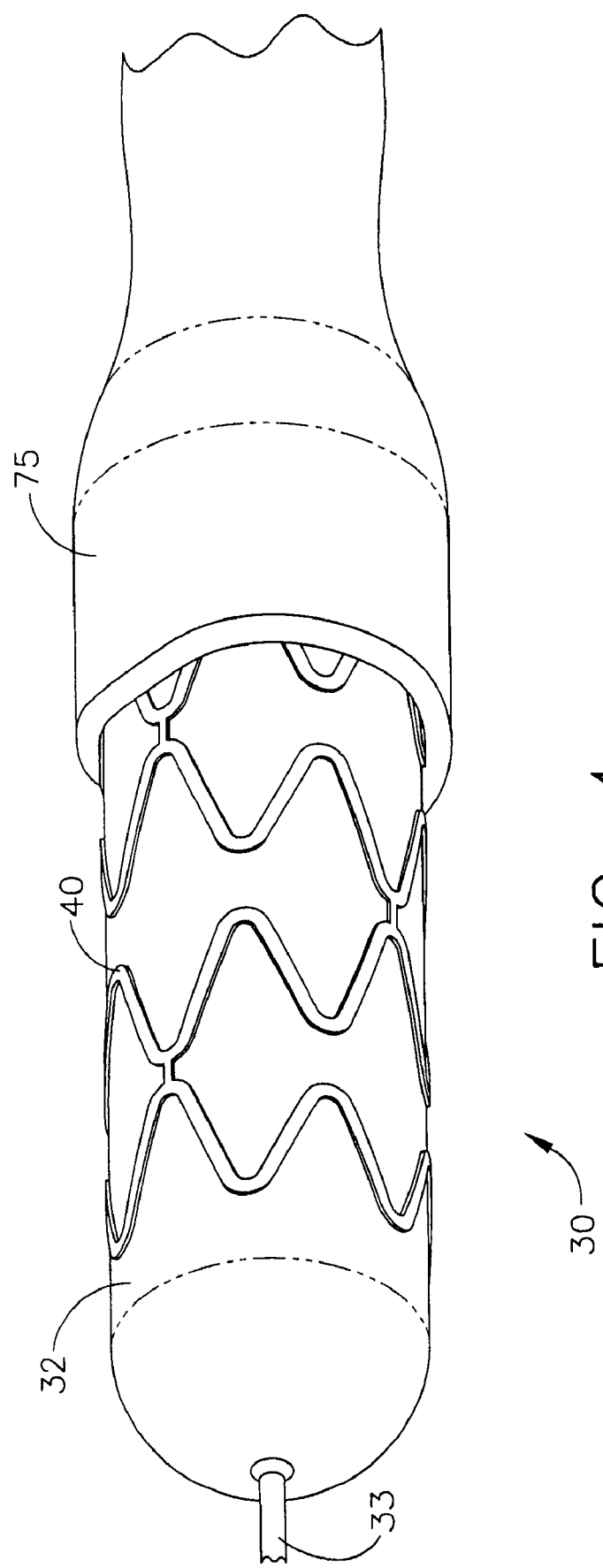
FIG. 4 is an isometric view of the portion of the anastomosis device of FIG. 3 shown extending from a first portion of intestine with the inflatable deployment device fully inflated to fully expand the stent.

The method of use of the anastomosis device proceeds as follows. The patient has been opened and a tumor has been found in a section of the jejunum. A portion of the jejunum containing the tumor and margins has been excised. The surgeon will now use the present invention to perform an end to end anastomosis of the two cut segments of the jejunum. In FIG. 2, the surgeon has inserted approximately half of the stent placement device 30 into a first portion 75 of the severed jejunum. In FIG. 3, the surgeon has partially inflated the balloon 32 by one or more strokes of the plunger 38 of the pump assembly 34. As the balloon enlarges, the radially outward pressure of the expanding balloon permanently expands the stent 40 to the size shown. In FIG. 4, the balloon 32 and stent 40 have been fully expanded by multiple strokes of the plunger 38 to a size deemed adequate by the surgeon, a size wherein the inner diameter of the stent 40 is slightly larger than the inner diameter of the first portion 75 of jejunum.

Figure 5:
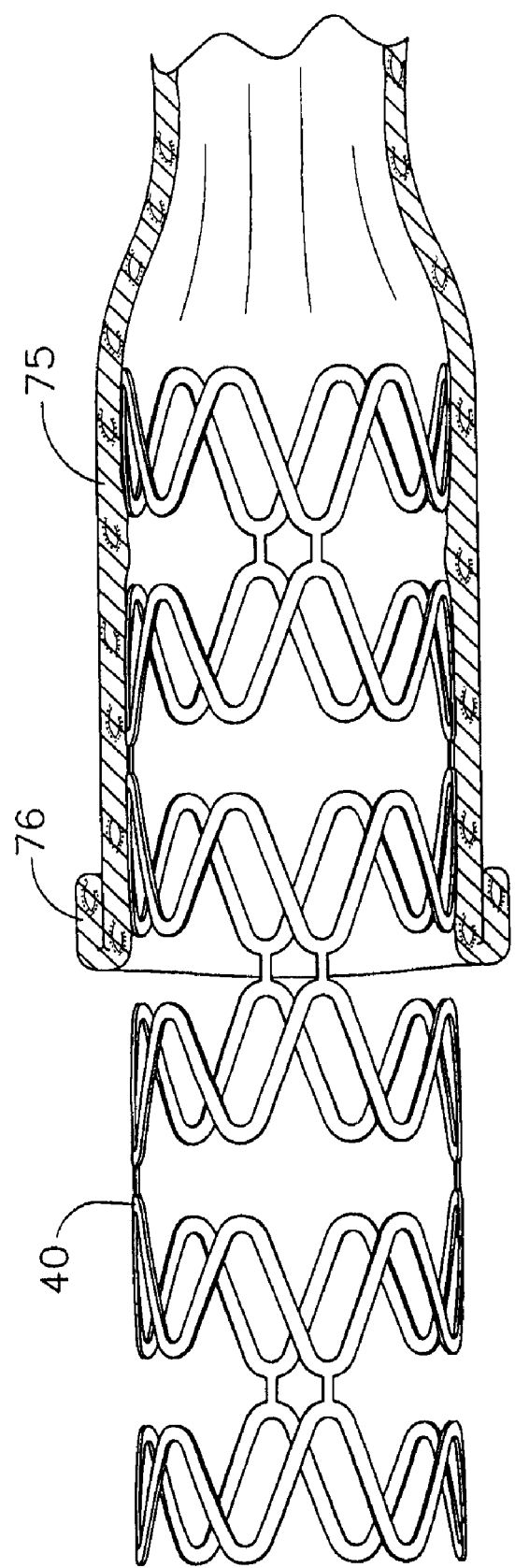
FIG. 5 is a side cross sectional view showing the fully expanded stent partially within the first portion of intestine after the inflatable deployment device has been deflated and removed, and showing a lip of the first portion of intestine everted over on itself.

In FIG. 5, the stent 40 is fully expanded to the selected diameter and the balloon 32 and hollow catheter 33 have been removed. Once deployed the stent 40 applies a radial pressure on the jejunum opening, both keeping it open and allowing for easy manipulation during the procedure. To remove the balloon 32 and hollow catheter 33, the surgeon has actuated the release valve 39 to vent the pressurized air within the balloon 32 to atmospheric, has applied a vacuum to the venting passageway 36a to deflate the balloon 32, and removed the deflated balloon 32 and catheter 33 from within the stent 40. The surgeon has also everted or folded the free end of the first portion 75 of jejunum over to create an everted tissue fold 76 exposing the inside layer of the tissue in an external radial fashion as shown.

Figure 6:
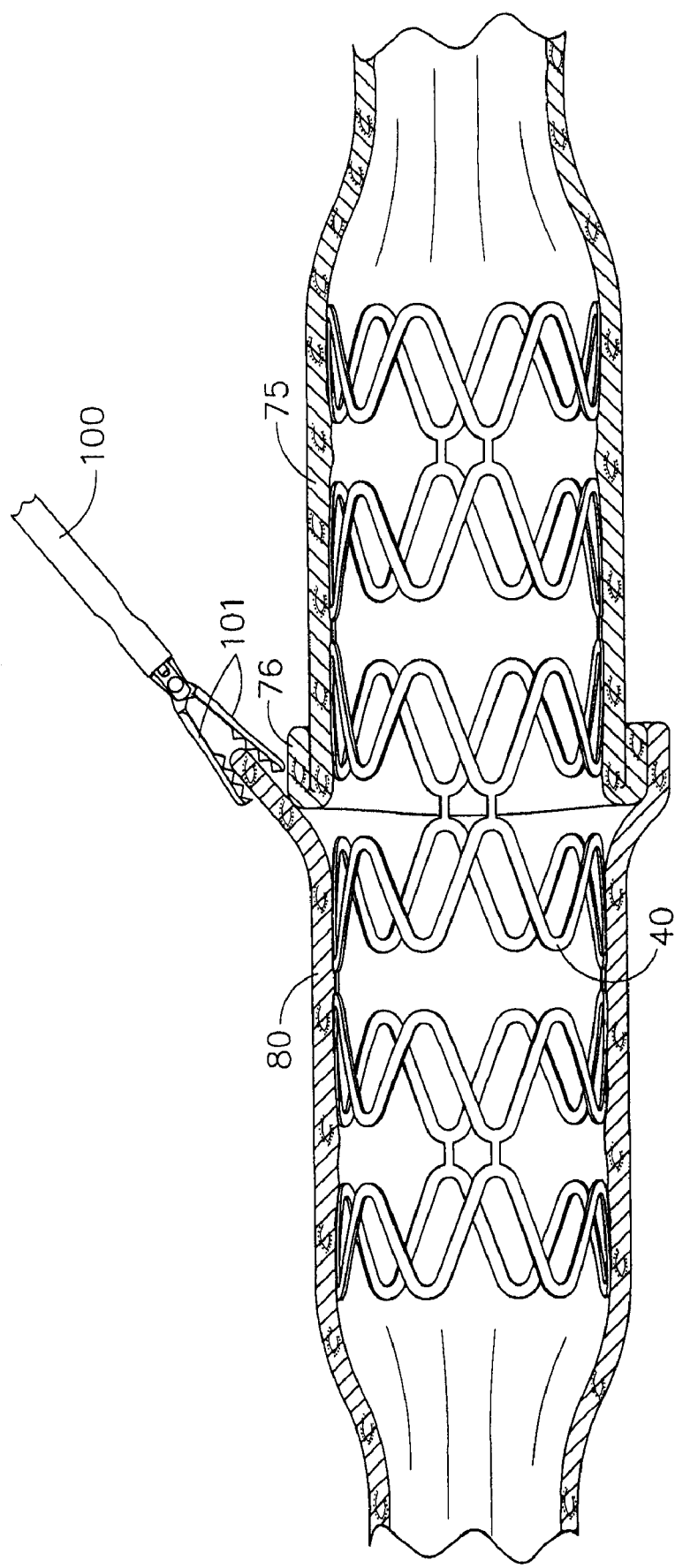
FIG. 6 is a side cross sectional view of FIG. 5 showing a grasper pulling a second portion of intestine onto the fully expanded stent and over the everted lip of the first portion of intestine.

Now turning to FIG. 6, the second portion 80 of the jejunum is grasped between jaws 101 of a grasper 100 then pulled over both the remaining part of the stent 40 and the rolled first tissue fold 76 of jejunum 75. This action places the inside of the first portion 75 of jejunum in direct contact with the inside of the adjacent second portion 80 of jejunum.

Figure 7:
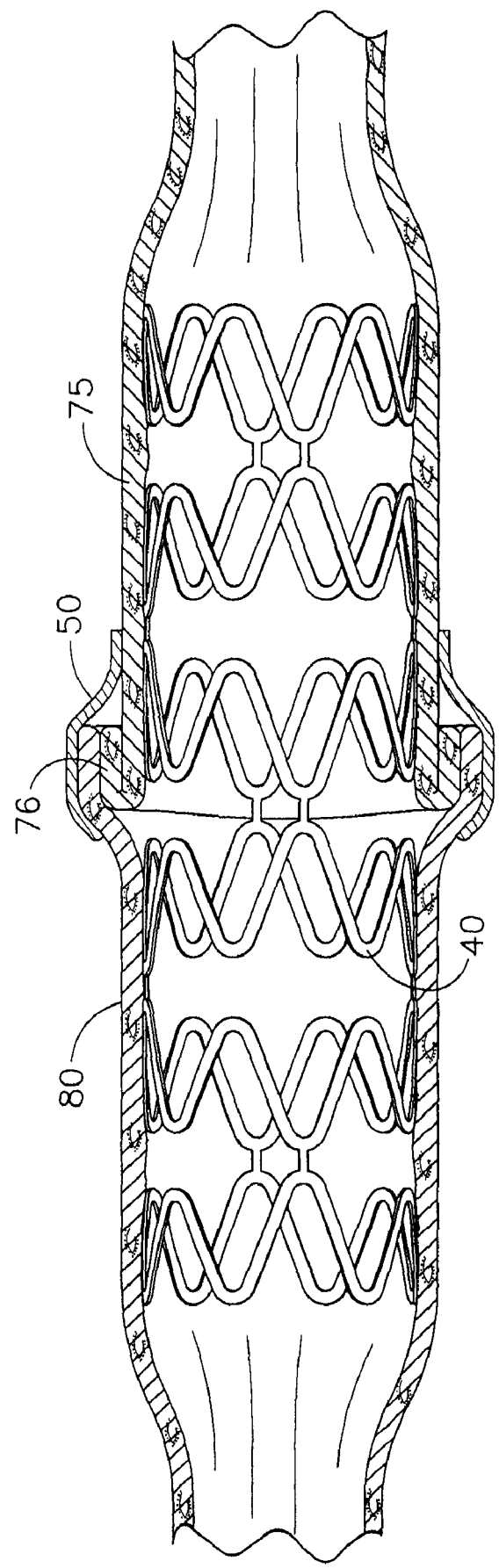
FIG. 7 is a side cross sectional view of FIG. 6 showing a layer of adhesive saturated material placed around the overlapping joint of the first portion and second portion of intestine.

A radial layer of bandage 50 is then placed in a continuous band of one or more layers around the first portion 75 of jejunum, the second portion 80 of jejunum, and around the everted first tissue fold 76 as shown in FIG. 7. Bandage 50 is impregnated with an adhesive initiator to induce polymerization of an adhesive. The adhesive initiator and bandage 50 are generally dry, and bandage 50 can be repositioned any number of times until the surgeon is satisfied with the placement.

Figure 8:
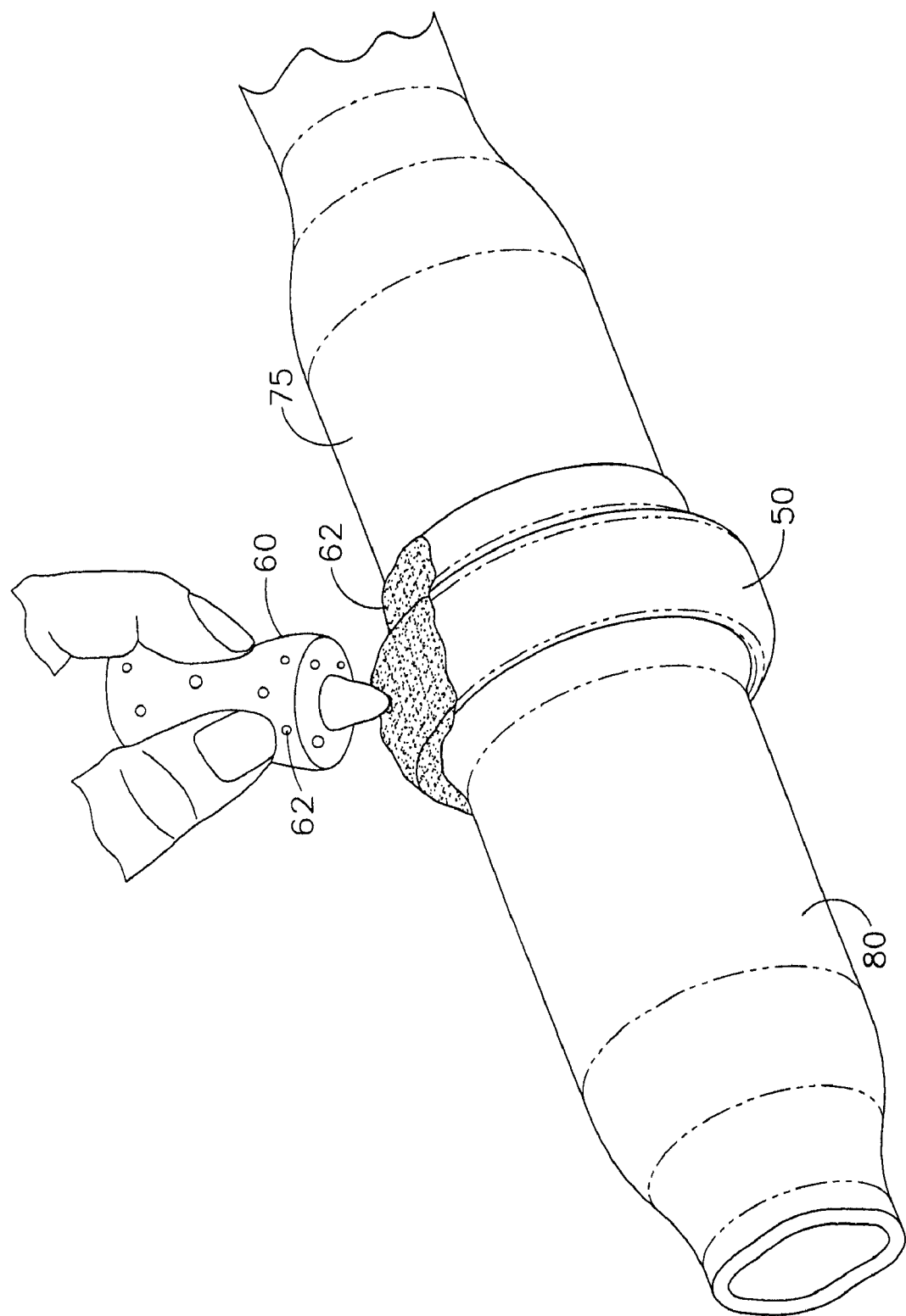
FIG. 8 is an isometric view of the completed anastomosis of the first portion and second portion of intestine with the inner layers in contact to ensure tissue growth, and with the adhesive saturated material creating a leak proof joint between the intestinal portions.

Once the bandage 50 has been placed in position, the dispenser 60 is opened by breaking the cap 63 off. As shown in FIG. 8 adhesive 62 is applied onto the bandage 50 from the dispenser 60. Only enough adhesive 62 is used to saturate the bandage 50 until the tissue below is in contact with the adhesive 62. The adhesive initiator on the bandage 50 ensures curing of the adhesive 62 is nearly instantaneous. The rapid curing prevents adhesive 62 from dripping, and prevents bandage 50 from adhering to adjacent structures inadvertently. If desired, after applying the adhesive 62, the surgeon can use dye or pressure to check for leaks, and if required, a simple touch-up of adhesive 62 is used to block the leaks.

In an alternate embodiment of the method, one could perform a mucosal to mucosal anastomosis by inverting the mucosa of one tissue portion onto the active stent adhesive and pulling the second tissue portion with its mucosa likewise inverted over the stent and first leg. All other steps being equivalent In an alternate embodiment of the device, the bandage 60 can contain the adhesive 62 and the dispenser 60 can contain an adhesion initiator. Application of adhesive initiator onto the bandage 50 sets the adhesive 62.

Also, expanding/foaming adhesives can also be used that would further insure the adhesion of all of the structures, even in the folds of the jejunum.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, whereas the stent placement device described above is a balloon 33, the stent 40 could be formed from a shape memory alloy such that the stent placement device is the body temperature that makes the stent constructed from the shape memory alloy undergo a phase change and revert to a larger diameter. Alternately, heating devices such as resistive heaters could be used to as the stent placement device, or a series of interlocking expanding wedges or any other device or means that can change a cylindrical stent from a small diameter to a larger diameter.

What is claimed is:

1. A method of creating an end-to-end anastomosis between a first portion of intestinal tissue having a first cross-sectional opening and a second portion of intestinal tissue having a second cross-sectional opening, wherein the method comprises:
   a) inserting an expandable biodegradable stent and a stent expansion device located inside the expandable biodegradable stent longitudinally into the first cross-sectional opening;
   b) expanding the stent expansion device to expand the stent in the first portion of intestinal tissue;
   c) everting an end of the first portion of intestinal tissue on the expanded stent such that the entire everted portion radially folds back and directly contacts the exterior surface of the first portion of intestinal tissue;
   d) removing the stent expansion device from the expanded stent, such that the expanded stent remains within the first portion of intestinal tissue, wherein during the act of removing the stent expansion device, the entire everted portion remains in direct contact with the exterior surface of the first portion of intestinal tissue;
   e) drawing the end of the second portion of intestinal tissue over the everted end to create an overlapping joint, wherein during the act of drawing the end of the second portion, the entire everted portion remains in direct contact with the exterior surface of the first portion of intestinal tissue;
   f) wrapping the overlapping joint with a bandage containing an adhesive, wherein during the act of wrapping the overlapping joint, the entire everted portion remains in direct contact with the exterior surface of the first portion of intestinal tissue; and
   g) securing the first portion and the second portion of intestinal tissue together in an anastomosis by saturating the bandage with an adhesive initiator applied using an applier to initiate adhesion of the first portion of intestinal tissue and the second portion of intestinal tissue to the bandage, wherein the expanded stent remains within the first portion of intestinal tissue after the act of saturating the bandage, wherein the expanded stent is configured to permit fluid communication from the first portion of intestinal tissue to the second portion of intestinal tissue through the expanded stent, wherein during the act of securing the first portion and the second portion of intestinal tissue together, the entire everted portion remains in direct contact with the exterior surface of the first portion of intestinal tissue.

2. The method recited in claim 1, further comprising the step of checking the anastomosis for leaks.

3. The method recited in claim 2 further including the step of resealing the leaks with a re-application of the adhesive and the adhesive initiator.

4. The method recited in claim 3 further including the step of removing the stent from the anastomosis by biodegrading the stent after the first and second portions of tissue grow together.

5. The method recited in claim 1, wherein the step of drawing the end of the second portion of intestinal tissue over the everted end includes the step of placing an inner surface of the second portion of intestinal tissue into contact with the exposed inner surface of the everted end of the first portion of intestinal tissue.

6. The method recited in claim 1, wherein the adhesive comprises a polymer adhesive, wherein the step of securing the first portion and the second portion of intestinal tissue together includes the step of polymerizing the adhesive with a polymerization initiator.

7. The method recited in claim 1, wherein the stent expansion device is a balloon and the step of removing the stent expansion device includes the step of deflating the balloon prior to removing the stent expansion device.

8. The method of claim 1, wherein the stent is made from one or more bioabsorbable materials selected from the group of polylactic acid, polyglycolic acid, polyglactin, polydioxanone, and polyglyconate.

9. The method of claim 1, wherein the bandage is made from one or more bioabsorbable materials selected from the group of polylactic acid, polyglycolic acid, polyglactin, polydioxanone, polyglyconate, whey protein, cellulose gum, starch, gelatin and polydioxanone.

10. The method of claim 1, wherein the adhesive is made from one or more bioabsorbable materials selected from the group consisting of a polymerizable monomer, a polymerizable 1,1-disubstituted ethylene monomer, and a cyanoacrylate formulation.

11. The method of claim 1, wherein the adhesive initiator is made from one or more bioabsorbable materials selected from the group of moisture, detergent compositions, surfactants, phosphines, phosphites, phosphonium salts, alcohols inorganic bases, inorganic salts, sulfur compounds, cyclic carbonates, acyclic carbonates, organometallics, radical initiators, and radicals.

* * * * *